United States Patent [19]

Hoffman

[11] Patent Number: 4,665,091
[45] Date of Patent: May 12, 1987

[54] MACROCYCLIC LACTONE HMG-COA REDUCTASE INHIBITORS

[75] Inventor: William F. Hoffman, Lansdale, Pa.

[73] Assignee: Merck & Co., Inc., Rahway, N.J.

[21] Appl. No.: 794,982

[22] Filed: Nov. 4, 1985

[51] Int. Cl.[4] .................. C07D 321/00; A61K 31/365
[52] U.S. Cl. ..................................... 514/450; 549/267
[58] Field of Search ........................ 549/267; 514/450

[56] References Cited

U.S. PATENT DOCUMENTS 4,239,690 12/1980 Gurusiddaiah et al. ............ 549/267

Primary Examiner—Jane T. Fan
Attorney, Agent, or Firm—Joseph F. DiPrima; Michael C. Sudol

[57] ABSTRACT

Novel 3-hydroxy-3-methylglutaryl-coenzyme A (HMG-CoA) reductase inhibitors which are useful as antihypercholesterolemic agents and are represented by the following general structural formula (I):

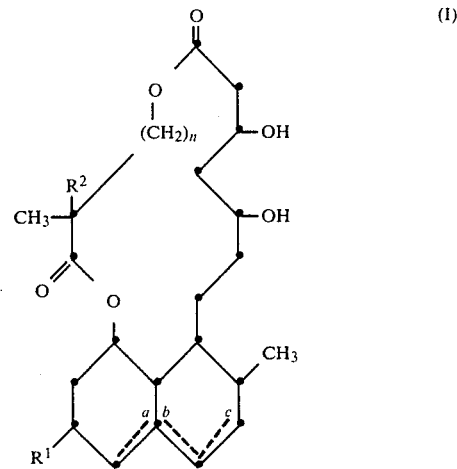

are disclosed. Also disclosed are pharmaceutical compositions and methods of use of the compounds of formula (I).

8 Claims, No Drawings

MACROCYCLIC LACTONE HMG-COA REDUCTASE INHIBITORS

BACKGROUND OF THE INVENTION

Hypercholesterolemia is known to be one of the prime risk factors of cardiovascular disease such as arteriosclerosis, and there is still no effective antihypercholesterolemic agent commercially available that has found wide patient acceptance. The bile acid sequestrants seem to be moderately effective but they must be consumed in large quantities, i.e. several grams at a time and they are not very palatable.

There are agents known, however, that are very active antihypercholesterolemic agents that function by limiting cholesterol biosynthesis by inhibiting the enzyme, HMG-CoA reductase. These agents include the natural fermentation products compactin and mevinolin and a variety of semi-synthetic and totally synthetic analogs thereof.

The naturally occurring compounds and their semi-synthetic analogs have the following general structural formulae:

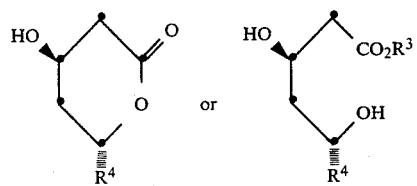

wherein
$R^3$ is hydrogen, $C_{1-5}$ alkyl or $C_{1-5}$ alkyl substituted with a member of the group consisting of phenyl, dimethylamino, or acetylamino;
$R^4$ is:

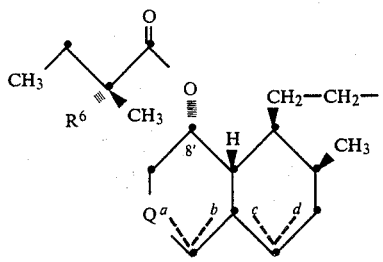

wherein
Q is

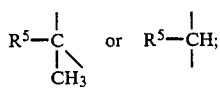

$R^5$ is H or OH: provided that when a is a double bond Q is

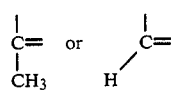

$R^6$ is hydrogen or methyl; and a, b, c, and d represent optional double bonds, especially where b and d represent double bonds or a, b, c, and d are all single bonds.

SUMMARY OF THE INVENTION

This invention relates to novel compounds which are HMG-CoA reductase inhibitors and are useful as antihypercholesterolemic agents. Specifically, the compounds of this invention are semi-synthetic analogs of compactin and mevinolin and the dihydro and tetrahydro analogs thereof which possess a macrocyclic lactone moiety and not the 6-membered lactone function, 4(R)-hydroxy-3,4,5,6-tetrahydro-2H-pyran-2-one, which is characteristic of the known HMG-CoA reductase inhibitors. Additionally, pharmaceutical compositions of these novel compounds, as the sole therapeutically active ingredient, and in combination with bile acid sequestrants are disclosed.

DETAILED DESCRIPTION OF THE INVENTION

The specific HMG-CoA reductase inhibitors of this invention are the compounds represented by the following general structural formula (I):

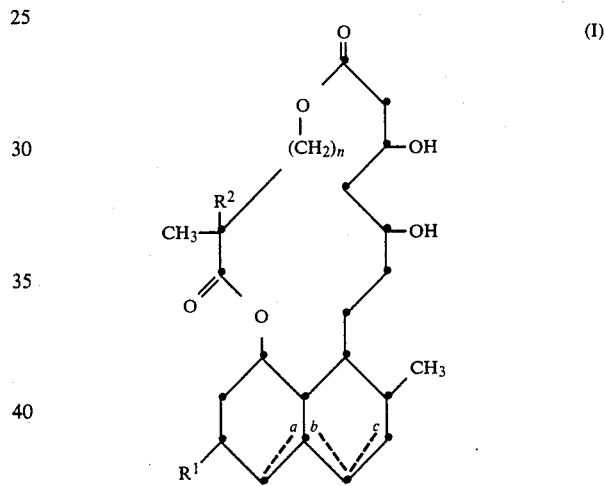

wherein
n is 0 to 5;
$R^1$ and $R^2$ independently are hydrogen or methyl; and the dotted lines at a, b and c represent optional double bonds, especially where one of a, b and c is a double bond, all of a, b and c are single bonds or a and c are double bonds.

A preferred embodiment ot this invention is the class of compounds of the formula (I) wherein n is 1 to 3. A sub-class of these compounds is exemplified by the compounds containing two double bonds at a and c or a, b, and c are all single bonds.

A more preferred embodiment of this invention is the class of compounds of the formula (I) wherein n is 1 to 3; $R^2$ is methyl; all of a, b and c are single bonds or a and c are double bonds. The two sub-classes of these compounds are exemplified by the compounds wherein $R^1$ is hydrogen or methyl.

The most preferred embodiment of this invention is the class of compounds of the formula (I) wherein n is 1 to 3; $R^1$ and $R^3$ are methyl; and the dotted lines at a and c are representative of double bonds. Exemplifying this embodiment is 10R-(10R*,12R*,14aS*,15S*,19R*,20 aS*,20bR*)-3,4,5,6,9,10,11,12,13,14,14a,15,19,20a,20b- hexadecahydro-10,12-dihydroxy-3,3,15,19-tetramethyl-2H,8H-naphtho(1,8-HI)-1,7-dioxacycloheptadecin-2,8-dione.

The compounds of formula (I) are conveniently prepared from compactin, mevinolin or the appropriate dihydro or tetrahydro analog thereof via the following general synthetic pathway:

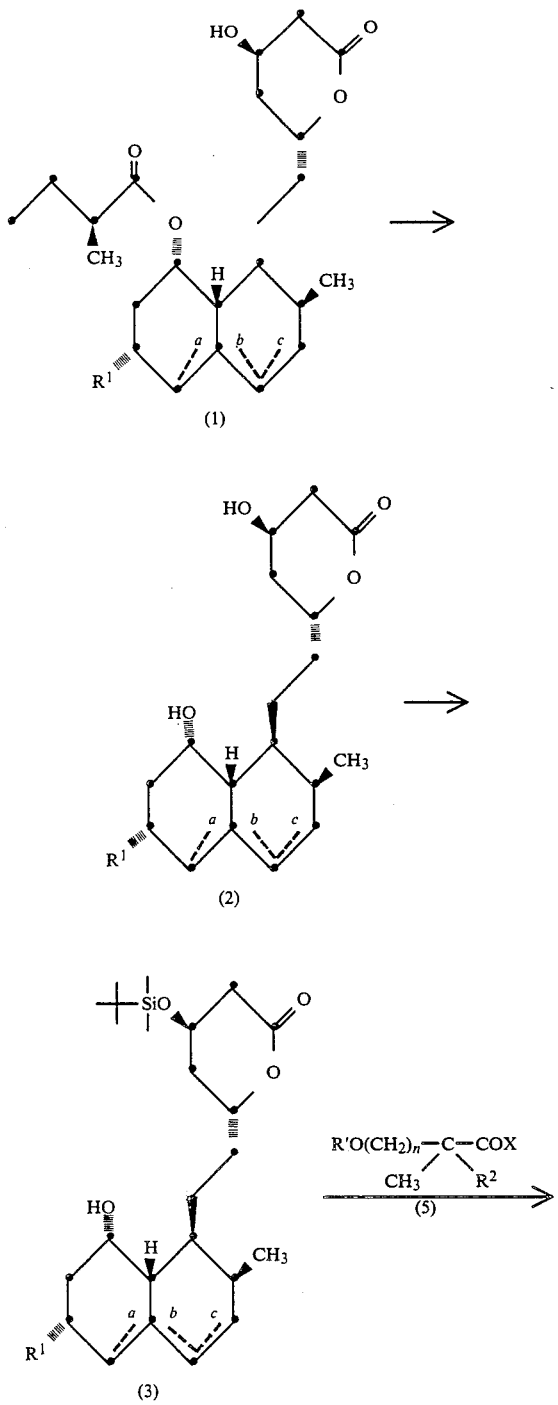

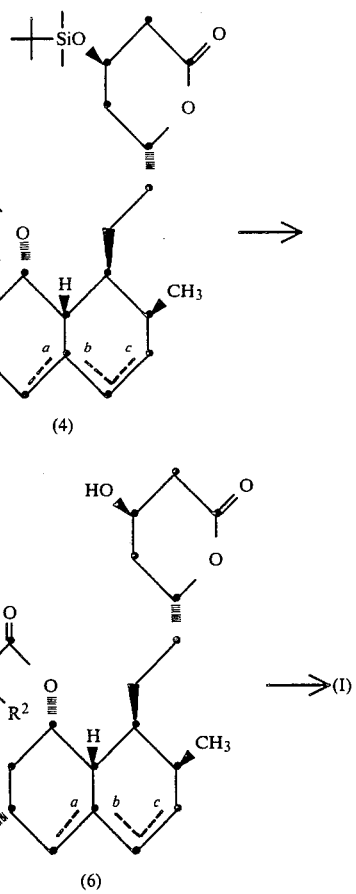

The starting materials compactin, mevinolin and their dihydro and tetrahydro analogs are readily available or may be prepared according to fermentation procedures disclosed in U.S. Pat. No. 3,983,140, U.S. Pat. No. 4,049,495, U.S. Pat. No. 4,231,938, and U.S. Pat. No. 4,294,846 and the hydrogenation procedures disclosed in U.S. Pat. No. 4,351,844. The appropriate starting material of formula (1) is then hydrolyzed under the conditions disclosed in U.S. Pat. No. 4,444,784 to afford the compounds of formula (2). The 4-hydroxy function in the lactone moiety of the compounds of formula (2) is protected with a suitable protecting agent, exemplified here as a dimethyl-t-butylsilyl group, according to the procedure disclosed in U.S. Pat. No. 4,444,784. Acylation of the 8' hydroxy group of the compounds of the formula (3) is accomplished under suitable conditions utilizing the appropriately substituted acid halides of the formula (5) wherein n and $R^2$ are as described above, X is chloro or bromo, preferably chloro, and R' is a suitable protecting group such as $$\underset{(C_{1-5}alkyl)C-}{\overset{O}{\parallel}}$$

to afford the compounds of the formula (4). The protecting group at the 4-position of the lactone moiety of the compounds of formula (4) is removed utilizing suitable conditions to afford the compounds of the formula (6).

The compounds of formula (6) are treated with an alkali metal hydroxide, such as sodium hydroxide, to convert the lactone moiety into an alkali metal salt of 3,5 dihydroxycarboxylate (ring opened form) and to remove the acyl protecting group, R', followed by treatment with dilute mineral acid, such as 10% hydrochloric acid, to form the free trihydroxy carboxylic acid. Macrocyclic lactonization is conducted under azeotropic conditions, such as refluxing toluene. The desired compounds of the formula (I) are purified by chromatography.

The appropriately substituted acid halides of the formula (5) are conveniently prepared from known starting material utilizing standard chemical transformations.

The synthesis of these compounds of the formula (5) wherein n is 2 or 3 is accomplished as follows:

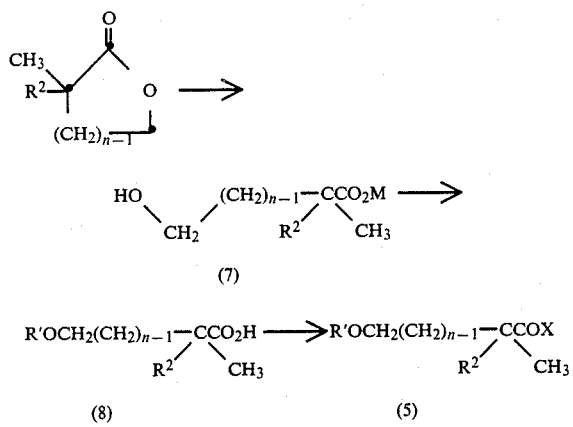

Specifically, when n is 2, dihydro-3-methyl-2(3H)furanone or dihydro-3,3-dimethyl-2(3H)furanone is treated with an alkali metal hydroxide, such as sodium hydroxide, followed by acrylation with a $C_{2-6}$ alkanoyl anhydride, such as acetic anhydride and the resulting carboxylic acid of the formula (8) is then treated with an acid halide-forming agent, such as oxalyl chloride, to yield the desired acid halide of the formula (5). For the compounds of the formula (5) wherein n is 3, the analogous starting materials tetrahydro-3-methyl-2(2H)pyranone or tetrahydro-3,3-dimethyl-2(2H)pyranone are used.

The synthesis of the compounds of formula (5) wherein n is 1 is started from the readily available 3-hydroxypropionic acids of the formula (7).

The compounds of this invention are useful as antihypercholesterolemic agents or pro-drugs thereof for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg to 2000 mg (preferably 2 to 100 mg) which may be given in two to four divided doses. Higher doses may be favorably employed as required.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:1 and 1:15,000.

Included within the scope of this invention is the method of treating arteriosclerosis, familial hypercholesterolemia or hyperlipidemia which comprises administering to a subject in need of such treatment a nontoxic therapeutically effective amount of the compounds of formula (I).

The following examples illustrate the preparation of the compounds of the formula (I) and their incorporation into pharmaceutical compositions and as such are not to be considered as limiting the invention set forth in the claims appended hereto.

EXAMPLE 1

Preparation of 6(R)-[2-[8(S)-(4-Acetyloxy-2,2-dimethyl-butyryloxy)-2(S),6(R)-dimethyl-1,2,6,7,8,8a-(R)-hexahydronaphthyl-1(S)]ethyl]-4(R)-hydroxy-3,4,5,6-tetrahydro-2H-pyran-2-one (a)

6(R)-[2-[8(S)-Hydroxy-2(S),6(R)-dimethyl-1,2,6,7,8,8a(R)-hexahydronaphthyl-1(S)]-ethyl]-4(R)-hydroxy-3,4,5,6-tetrahydro-2H-pyran-2-one (2)

A mixture of 20.0 g (49.4 mmol) of mevinolin and 20.7 g (0.493 mol) of LiOH H$_2$O in 1.5 L of water was stirred at reflux for 72 hours. The reaction mixture was cooled to 0° C., acidified by addition of 50 ml of conc HCl and then extracted with ether (3×500 ml). The combined extracts were washed with water (3×500 ml) and satd. brine (500 ml), dried (MgSO$_4$) and evaporated to give a white solid. This solid was dissolved in 300 ml of toluene and heated at reflux for 2 hours in a Dean-Stark apparatus for azeotropic removal of water. After evaporation of the toluene, the residual oily solid was heated at reflux in hexane (150 ml) for 30 minutes. After cooling to 0° C., the hexane solution was filtered and the collected solid was dried in air to yield an off-white powder. An analytical sample was prepared by recrystallization of a portion of this material from 1-chlorobutane to give white clusters: m.p. 128°–131° C. (vac).

Anal. Calc'd for C$_{19}$H$_{28}$O$_4$.0.1C$_4$H$_9$Cl: C, 70.67; H, 8.84. Found: C, 70.77; H, 8.75.

(b)

6(R)-[2-[8(S)-Hydroxy-2(S),6(R)-dimethyl-1,2,6,7,8,8a(R)-hexahydronaphthyl-1(S)]-ethyl]-4(R)-tert-butyldimethylsilyloxy-3,4,5,6-tetrahydro-2H-pyran-2-one A mixture of 18.3 g (57.1 mmol) of alcohol from Example 1(a), 12.9 g (85.6 mmol) of tert-butyldimethylchlorosilane and 11.6 g (171.2 mmol) of imidazole in 200 ml of DMF was stirred at 20° C. for 18 hours. The reaction mixture was diluted with 1.5 L of ether and washed successively with water, 2% aq HCL, water and satd. aq NaHCO$_3$. The ether solution was dried (MgSO$_4$), filtered and reduced to one liter. After addition of 600 ml of hexane, the volume was reduced to 600 ml on a steam bath. Crystallization at room temperature provided the silyl ether as a white, cottony solid: m.p. 142°–144° C. (vac).

Anal. Calc'd for C$_{25}$H$_{42}$O$_4$Si: C, 69.08; H, 9.74. Found: C, 69.46; H, 9.83.

(c) Dihydro-3,3-dimethyl-2(3H)furanone[1]

The dihydro-3-methyl-2(3H)furanone (10.0 g, 0.1 mol) was slowly added to a cold (−78° C.), THF solution (150 ml) of LDA (0.11 mol) so that the internal temperature did not exceed −65° C. After stirring for an additional 30 minutes, the acetone/$CO_2$ bath was replaced with a $CH_3CN/CO_2$ bath and $CH_3I$ (21.3 g, 0.15 mol) was added at a rate sufficient to maintain the internal temperature at −30° C. After stirring at −30° C. for another hour the reaction mixture was allowed to warm to 0° C. and quenched by the dropwise addition of 10% HCl (40 ml, 0.116 mol). The resulting mixture was poured into ether (700 m) and the ether layer was washed with brine (2×50 ml), dried ($MgSO_4$), and evaporated to a yellow oil. The oil was distilled to give desired product as a colorless liquid, bp$_{18}$ 80°–82° C.

[1] Klunt, W. E.; Covey, D. F., Ferrendelli, J. A., Mol. Pharmacol. 22, 438–443, 1982.

(d) 2,2-Dimethyl-4-hydroxybutanoic acid sodium salt

A solution of 1N NaOH (89 ml, 89 mmol) and the lactone from Example 1(c) (10.0 g, 87.6 mmol) in methanol (50 ml) was stirred at ambient temperature for 18 hours. The solution was concentrated to dryness in vacuo (bath temperature 50° C.). The residue was suspended in toluene (2×50 ml) and the toluene evaporated in vacuo to provide sodium salt as a white powder.

(e) 4-Acetyloxy-2,2-dimethylbutanoic acid

A mixture of the sodium salt from Example 1(d) (5.3 g, 34.4 mmol) and 4-pyrrolidinopyridine (1 g, 6.9 mmol) in pyridine (20 ml) was cooled to 0° C. (ice/acetone bath). After the acetic anhydride (7.02 g, 68.8 mmol) was added, the cooling bath was removed and the reaction mixture was stirred at ambient temperature for 18 hours. The reaction mixture was cooled to 0° C., acidified with 6N HCl, saturated with NaCl and extracted with ether (3×50 ml). The combined extracts were washed with saturated brine (3×25 ml), dried ($MgSO_4$), and evaporated to give a pale yellow liquid. A NMR spectrum showed that this liquid was a mixture of the acid and lactone. An ether solution of the mixture was extracted with saturated $NaHCO_3$ solution (4×10 ml). The combined extracts were acidified with 6N HCl, and the resulting mixture extracted with ether (3×50 ml). The combined ether extracts were dried ($MgSO_4$), and evaporated to give a pale yellow oil which was distilled to provide the acid as a colorless liquid: bp$_{0.5}$ 103°–104° C.

(f) 4-Acetyloxy-2,2-dimethylbutyrylchloride

A solution of the acid from Example 1(e) (14.0 g, 80.4 mmol), oxalyl chloride (11.2 g, 88.4 mmol) and DMF (4 drops) in benzene (50 ml) was stirred at ambient temperature for 1 hour. The light red solution was distilled to provide the acid chloride as a colorless liquid: bp$_{0.5}$ 72°–74° C.

(g) 6(R)-[2-[8(S)-(4-Acetyloxy-2,2-dimethylbutyryloxy)-2(S),6(R)-dimethyl-1,2,6,7,8,8a(R)-hexahydronaphthyl-1(S)]ethyl]-4(R)-tert-butyldimethylsilyloxy-3,4,5,6-tetrahydro-2H-pyran-2-one A stirred solution of the alcohol from Example 1(b) (8.9 g, 20.5 mmol), 4-pyrrolidinopyridine 610 mg, 4.1 mmol) and the acid chloride from Example 1(f) (3.9 g, 20.5 mmol) in pyridine (50 ml) was heated under a nitrogen atmosphere at 100° C. After 2 hours, 4 hours and 10 hours, another 1.95 g of the acid chloride was added and the reaction solution was stirred for a total of 18 hours. After cooling to 60° C., the pyridine was removed (in vacuo) and the residue was diluted with ether (500 ml). The resulting mixture was washed with 1N HCl (2×25 ml), satd. $NaHCO_3$ solution (25 ml), satd. brine (2×50 ml) and dried ($MgSO_4$). Evaporation of the ether solution gave the crude product as a yellow liquid. This liquid was chromatographed on a 17.5×7 cm column of silica gel (230–400 mesh). Elution (under air pressure) with acetone-methylene chloride (1:99, v:v) provided the ester contaminated with acid and acid chloride which was used in the next step without further purification.

(h) 6(R)-[2-[8(S)-(4-Acetyloxy-2,2-dimethylbutyryloxy)-2(S),6(R)-dimethyl-1,2,6,7,8,8a(R)-hexahydronaphthyl-1(S)ethyl]-4(R)-hydroxy-3,4,5,6-tetrahydro-2H-pyran-2-one A solution of the crude ester from Example 1(g) (12.3 g, 20.8 mmol) in THF (100 ml) was treated with acetic acid (4.7 ml, 83.2 mmol) and a 1M solution of tetrabutylammonium fluoride in THF (62.4 ml, 62.4 mmol) and was stirred at ambient temperature for 20 hours. The reaction mixture was diluted with ether (500 ml) washed with 1.5N HCl (50 ml), satd. $NaHCO_3$ (50 ml) and satd. brine (2×50 ml) and dried ($MgSO_4$). The solvent was evaporated to provide a pale yellow oil which was used in the next step without further purification.

EXAMPLE 2

Preparation of 6(R)-[2-[8(S)-(4-Acetyloxy-2-methylbutyryloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one

(a) 2-Methyl-4-hydroxybutanoic acid sodium salt

Employing the procedure of Example 1(d) but using dihydro-3-methyl-2(3H)furanone (30 g, 0.3 mol) the title compound was obtained as a white solid and was used without further purification in the following step. NMR ($D_2O$) δ1.10 (3H, d, J=7H), 1.37–2.00 (2H, m), 2.18–2.57 (H, m), 3.60 (2H, t, J=7 Hz).

(b) 4-Acetoxy-2-methylbutanoic acid

Employing the procedure of Example 1(e) but using compound from Example 2(a) (38.7 g, 0.276 mol) the title compound was obtained as a pale yellow liquid. b.p.$_{0.1}$ 102°–105° C., NMR ($CDCl_3$) δ1.23 (3H, d, J=7 Hz), 1.60–2.27 (2H, m), 2.02 (3H, s), 2.43–2.50 (H, m), 4.10 (2H, t, J=7 Hz).

(c) 4-Acetoxy-2-methylbutyryl chloride

Employing the procedure of Example 1(f), but using the compound from Example 2(b) (9.2 g, 0.057 mol), the total compound was obtained as a colorless liquid, b.p.$_{0.3}$ 60°–61° C.

NMR ($CDCl_3$) δ1.33 (3H, d, J=7 Hz), 1.63–2.40 (2H, m), 2.03 (3H, s), 2.77–3.20 (H, m), 4.13 (2H, t, J=7 Hz).

(d) 6(R)-[2-[8(S)-(4-Acetyloxy-2-methylbutyryloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one Employing the general procedures in Example 1(g) through 1(h), the compound from Example 2(c) was converted into the title compound.

EXAMPLE 3

Preparation of 6(R)-[2-[8(S)-(3-Acetyloxy-2,2-dimethylpropionyloxy)-2(S),6(R)-dimethyl-1,2,6,7,8,8a-(R)-hexahydronapht-hyl-1(S)]ethyl]-4(R)-hydroxy-3,4,5,6-tetrahydro-2H-pyran-2-one (a) 3-Acetoxy-2,2-dimethylpropionic acid Acetyl chloride (4.52 g, 58.2 mmol) was added dropwise to a cold (0° C.) pyridine solution (10 ml) of 2,2-dimethyl-3-hydroxypropionic acid (5.5 g, 46.5 mmol) and 4-DMAP (0.57 g, 4.65 mmol). After stirring overnight at ambient temperature, the reaction was poured into ether (200 ml). This mixture was washed with 10% HCl (2×20 ml), and saturated brine (2×25 ml) and the resulting ethereal solution was dried (MgSO$_4$). Evaporation gave the title compound as a pale yellow solid which was used in the next step without further purification. NMR (CDCl$_3$) δ4.13 (2H, s), 2.08 (3H, s), 1.26 (6H, s).

(b) 3-Acetoxy-2,2-dimethylpropionyl chloride

A benzene solution (25 ml) of crude 3-acetoxy-2,2-dimethyl propionic acid from Example 3(a) (7.4 g, 46.5 mmol), oxalyl chloride (6.45 g, 51 ml) and DMF (2 drops) was stirred at ambient temperature for 3 hours. The pale yellow solution was distilled to provide the title compound as a colorless liquid. b.p.$_{15}$ 85°-88° C. NMR (CDCl$_3$) δ4.18 (2H, s), 2.08 (3H, s), 1.35 (6H, s).

(c) 6(R)-[2-[8(S)-(3-Acetyloxy-2,2-dimethylpropionyloxy)-2(S),6(R)-dimethyl-1,2,6,7,8,8a(R)-hexahydronaphthyl-1(S)]ethyl]-4(R)-hydroxy-3,4,5,6-tetrahydro-2-H-pyran-2-one Employing the general procedures in Example 1(g) through 1(h), the compound from Example 3(b) was converted into the title compound.

EXAMPLE 4

Preparation of 6(R)-[2-[8(S)-(5-Acetyloxy-2,2-dimethylpentanoyloxy)-2(S),6(R)-dimethyl-1,2,6,7,8,8a-(R)-hexahydronapht-hyl-1(S)]ethyl]-4(R)-hydroxy-3,4,5,6-tetrahydro-2H-pyran-2-one (a) 3-Methyltetrahydro-2H-pyran-2-one Tetrahydro-2-H-pyran-2-one (10.0 g, 0.10 mol) was slowly added to a cold (−78° C.) THF solution (100 ml) of LDA (0.11 mol) so that the internal temperature did not exceed −65° C. After stirring for an additional 30 minutes, the acetone/CO$_2$ bath was removed and CH$_3$I (21.3 g, 0.15 mol) was added dropwise. When the internal temperature reached −30° C. the reaction was placed in a CH$_3$CN/CO$_2$ bath to maintain the internal temperature at −35±5° C. After stirring for 1 hour, the reaction mixture was allowed to warm to 0° C. and was quenched by the dropwise addition of sat. NH$_4$Cl solution. The resulting mixture was poured into ether (300 ml) and the ether layer was separated and washed with H$_2$O (50 ml), 1N HCl (25 ml), saturated brine (2×50 ml), dried (MgSO$_4$) and evaporated to provide an orange oil. Distillation of the oil gave the title compound as colorless oil. b.p.$_{15}$ 103°-105° C. NMR (CDCl$_3$) δ4.32 (2H, m), 2.58 (H, m), 2.08 (H, m), 1.84 (2H, m), 1.52 (H, m), 1.26 (3H, d, J=7 Hz).

(b) 3,3-Dimethyltetrahydro-2H-pyran-2-one

The 3-methyltetrahydro-2H-pyran-2-one from Example 4(a) (5.6 g, 49.0 mmol) was slowly added to a cold (−78° C.) THF solution (50 ml) of LDA (54 mmol) so that the internal temperature did not exceed −65° C. After stirring for an additional 30 minutes, the acetone/CO$_2$ bath was replaced with a CH$_3$CN/CO$_2$ bath and CH$_3$I (10.4 g, 73.5 mmol) was added at a rate sufficient to maintain the internal temperature at −45° C. After stirring at 31 45° C. for an additinal hour the reaction was allowed to warm to −30° C. and quenched by the dropwise addition of 10% HCl (21 ml). The resulting mixture was poured into ether (300 ml) and the ether layer was washed with saturated brine (50 ml), saturated NaHCO$_3$ solution (20 ml), saturated brine (2×25 ml), dried (MgSO$_4$) and evaporated to provide a pale yellow oil. This oil was distilled to give the title compound as a colorless liquid. b.p.$_{0.2}$ 54° C. NMR (CDCl$_3$) δ4.34 (2H, m), 1.89 (2H, m), 1.75 (2H, m), 1.30 (6H, s).

(c) 2,2-Dimethyl-5-hydroxypentanoic acid sodium salt

Employing the procedure of Example 1(d), but using the compound from Example 4(b) (5.0 g, 39 mmol), the title compound was obtained as a white solid and was used without further purification in the following step. NMR (D$_2$O) δ3.57 (2H, m), 1.47 (4H, m), 1.10 (6H, s).

(d) 5-Acetyloxy-2,2-dimethylpentanoic acid Employing the procedure of Example 1(e), but using the compound from Example 4(c) (6.5 g, 38.6 mmol), the title compound was obtained as a colorless liquid. b.p.$_{0.2}$ 120°-124° C. NMR (CDCl$_3$) δ4.06 (2H, m), 2.06 (3H, s), 1.62 (4H, m), 1.22 (6H, s).

(e) 5-Acetyloxy-2,2-dimethylpentanoyl chloride

Employing the procedure of Example 1(f), but using the compound from Example 4(d) (2.4 g, 12.7 mmol), the title compound was obtained as a colorless liquid. b.p.$_{0.2}$ 72°-74° C. NMR (CDCl$_3$) δ4.06 (2H, m), 2.06 (3H, s), 1.68 (4H, m), 1.31 (6H, s).

(f) 6(R)-[2-[8(S)-(5-Acetyloxy-2,2-dimethylpentanoyloxy)-2(S),6(R)-dimenthyl-1,2,6,7-8,8a(R)-hexahydronaphthyl-1-(S)]ethyl]-4(R)-hydroxy-3,4,5,6-tetrahydro-2H-pyran-2-one Employing the general procedures in Example 1(g) through 1(h), the compound from Example 4(e) was converted into the title compound.

EXAMPLES 5 to 15

Utilizing the general procedures of Examples 1 to 4 the following compounds of the formula (6) in the following table are prepared from the appropriate acid chloride and compactin, mevinolin, and the dihydro and tetrahydro analogs thereof.

| Compound | n | R' | R¹ | R² | a | b | c |
|---|---|---|---|---|---|---|---|
| 5 | 5 | CH₃CO | CH₃ | CH₃ | db | — | db |
| 6 | 2 | CH₃CO | H | CH₃ | db | — | db |
| 7 | 3 | CH₃CO | CH₃ | CH₃ | — | db | — |
| 8 | 2 | CH₃CO | CH₃ | CH₃ | db | — | — |
| 9 | 1 | CH₃CO | CH₃ | CH₃ | — | — | db |
| 10 | 2 | CH₃CO | CH₃ | CH₃ | — | — | — |
| 11 | 4 | CH₃CO | H | CH₃ | db | — | db |
| 12 | 1 | C₃H₇CO | H | H | — | — | — |
| 13 | 5 | CH₃CO | H | CH₃ | — | db | — |
| 14 | 1 | CH₃CO | H | H | db | — | db |
| 15 | 3 | CH₃CO | H | CH₃ | db | — | db | db = double bond

EXAMPLE 16

Preparation of
10R-(10R*,12R*,14aS*,15S*,19R*,20aS*-20bR*)-3,4,5,6,9,10,11,12,13,14,14a,15,19,20,20a,20b-hexadecahydro-10,12-dihydroxy-3,3,15,19-tetramethyl-2H,8H-naphtho-(1,8-HI)-1,7-dioxacycloheptadecin-2,8-dione To a solution of the compound from Example 4(f)(2.2 g, 4.48 mmol) in methanol (30 ml) was added dropwise 1N sodium hydroxide (13.4 ml, 13.4 mmol) and the mixture was stirred at ambient temperature for two hours. The methanol was removed in vacuo and the residue dissolved in water (30 ml), cooled to 0° C. and acidified with 10% hydrochloric acid to yield a gummy solid. The solid was dissolved in diethyl ether (300 ml). The solution was washed with saturated sodium chloride (3×50 ml), dried over magnesium sulfate and the solvent removed in vacuo to afford a pale yellow viscous oil.

The oil was dissolved in toluene (250 ml) and the solution azeotropically reflux for five hours with the removal of water. The toluene was removed in vacuo and the residue chromatographed over silica gel eluted with 20% acetone in methylene chloride (1L), 25% acetone in methylene chloride (1L) and 30% acetone in methylene chloride (1L). Twenty milliliter fractions were collected. Fractions 45 to 65 were combined and the solvent removed in vacuo. The residue was chromatographed over silica gel eluted with 10% isopropyl alcohol in hexane (1L) and 20% isopropyl alcohol in hexane (1L). Twenty milliliter fractions were collected. Fractions 25 to 32 were combined, and concentrated to dryness to afford the desired product as a colorless solid. This solid was recrystallized from n-butylchloride/hexane to yield the desired product as colorless needles. m.p. 143.5°–145.5° C. NMR analysis confirms the structure.

Anal. Calc'd for $C_{26}H_{40}O_6$: C, 69.61; H, 8.99. Found: C, 69.50; H, 9.31.

EXAMPLES 17 to 30

Utilizing the general procedure of Example 16 the following compounds of the formula (I) are prepared from the appropriate compounds from Examples 1 to 3 and 5 to 15.

| Compound | n | R¹ | R² | a | b | c |
|---|---|---|---|---|---|---|
| 17 | 2 | CH₃ | CH₃ | db | — | db |
| 18 | 2 | CH₃ | H | db | — | db |
| 19 | 1 | CH₃ | CH₃ | db | — | db |
| 20 | 5 | CH₃ | CH₃ | db | — | db |
| 21 | 2 | H | CH₃ | db | — | db |
| 22 | 3 | CH₃ | CH₃ | — | db | — |
| 23 | 2 | CH₃ | CH₃ | db | — | — |
| 24 | 1 | CH₃ | CH₃ | — | — | db |
| 25 | 2 | CH₃ | CH₃ | — | — | — |
| 26 | 4 | H | CH₃ | db | — | db |
| 27 | 1 | H | H | — | — | — |
| 28 | 5 | H | CH₃ | — | db | — |
| 29 | 1 | H | H | db | — | db |
| 30 | 3 | H | CH₃ | db | — | db |

EXAMPLE 31

As a specific embodiment of a composition of this invention, 20 mg of the lactone from Example 16 is formulated with sufficient finely divided lactose to provide a total amount of 580 to 590 mg to fill a size 0 hard gelatin capsule.

What is claimed is:

1. A compound represented by the following structural formula (I):

wherein
n is 0 to 5;
R¹ and R² independently are hydrogen or methyl; and one of a, b and c independently represents a double bond, all of a, b and c represent single bonds or a and c represent double bonds.

2. A compound of claim 1 wherein n is 1 to 3.

3. A compound of claim 2 wherein all of a, b and c are single bonds; or a and c are double bonds.

4. A compound of claim 3 wherein R¹ is methyl; and R² is hydrogen.

5. A compound of claim 3 wherein both R¹ and R² are methyl.

6. A compound of claim 5 wherein n is 3; and a and c are double bonds.

7. A hypocholesterolemic, hypolipidemic pharmaceutical composition comprising a nontoxic therapeutically effective amount of a compound of claim 1 and a pharmaceutically acceptable carrier.

8. A method of treating hypercholesterolemia comprising the administration to a subject in need of such treatment a nontoxic therapeutically effective amount of a compound of claim 1.

* * * * *